US009504410B2

(12) United States Patent  
Gal (10) Patent No.: US 9,504,410 B2  
(45) Date of Patent: Nov. 29, 2016

(54) BAND-LIKE GARMENT FOR PHYSIOLOGICAL MONITORING

(75) Inventor: Yoav Gal, Berkeley, CA (US)

(73) Assignee: adidas AG, Herzogenaurach (DE)

( * ) Notice: Subject to any disclaimer, the term of this patent is extended or adjusted under 35 U.S.C. 154(b) by 1991 days.

(21) Appl. No.: 11/586,026

(22) Filed: Oct. 24, 2006

(65) Prior Publication Data

US 2008/0015454 A1    Jan. 17, 2008

Related U.S. Application Data

(63) Continuation-in-part of application No. 11/233,317, filed on Sep. 21, 2005, now Pat. No. 8,034,001.

(60) Provisional application No. 60/730,890, filed on Oct. 26, 2005.

(51) Int. Cl.
| | |
|---|---|
| *A61B 5/04* | (2006.01) |
| *A61B 5/113* | (2006.01) |
| *A41D 13/12* | (2006.01) |
| *A61B 5/0205* | (2006.01) |
| *A61B 5/0408* | (2006.01) |
| *A61B 5/00* | (2006.01) |

(52) U.S. Cl.
CPC ......... *A61B 5/1135* (2013.01); *A41D 13/1281* (2013.01); *A61B 5/02055* (2013.01); *A61B 5/04085* (2013.01); *A61B 5/6831* (2013.01)

(58) Field of Classification Search
CPC .................................................. A51B 5/1135
USPC .................................................. 600/534–536
See application file for complete search history.

(56) References Cited

U.S. PATENT DOCUMENTS

| | | |
|---|---|---|
| 3,534,727 A | 10/1970 | Roman |
| 3,731,184 A | 5/1973 | Goldberg et al. |
| 3,874,368 A | 4/1975 | Asrican |
| 3,926,177 A | 12/1975 | Hardway, Jr. et al. |
| 4,016,868 A | 4/1977 | Allison ................. 128/2.1 |
| 4,033,332 A | 7/1977 | Hardway, Jr. et al. |
| 4,102,331 A | 7/1978 | Grayzel et al. |
| 4,258,718 A | 3/1981 | Goldman |

(Continued)

FOREIGN PATENT DOCUMENTS

| | | |
|---|---|---|
| DE | 4214263 | 11/1993 |
| EP | 0262778 | 4/1988 |

(Continued)

OTHER PUBLICATIONS

Fahrenberg, "Origins and Developments of Ambulatory Monitoring and Assessment", in Fahrenberg et al., 2001, Progress in Ambulatory Assessment. Seattle, WA: Hogrefe and Huber.

(Continued)

*Primary Examiner* — Christian Jang  
(74) *Attorney, Agent, or Firm* — Sterne, Kessler, Goldstein & Fox P.L.L.C.

(57) ABSTRACT

This invention provides a physiological monitoring garment having a band-like configuration and incorporating respiratory, cardiac and temperature sensors. The garment is designed so that it is easily constructed from a few number of separate elements, and so that one garment design can be adjusted to subjects of a range of sizes and shapes. The design is further adapted to require little on no wearer effort during donning or wearer attention during use.

22 Claims, 7 Drawing Sheets

(56) References Cited

U.S. PATENT DOCUMENTS

| | | | |
|---|---|---|---|
| 4,267,845 A | 5/1981 | Robertson, Jr. et al. | |
| 4,289,142 A | 9/1981 | Kearns | |
| 4,306,567 A | 12/1981 | Krasner | 600/484 |
| 4,308,872 A | 1/1982 | Watson et al. | 128/725 |
| 4,373,534 A | 2/1983 | Watson | 128/725 |
| 4,387,722 A | 6/1983 | Kearns | |
| 4,433,693 A | 2/1984 | Hochstein | 128/721 |
| 4,446,872 A | 5/1984 | Marsoner et al. | |
| 4,452,252 A | 6/1984 | Sackner | 128/671 |
| 4,456,015 A | 6/1984 | Sackner | 128/721 |
| 4,463,764 A | 8/1984 | Anderson et al. | 600/532 |
| 4,494,553 A * | 1/1985 | Sciarra et al. | 600/534 |
| 4,537,196 A | 8/1985 | Phillipps et al. | |
| 4,545,376 A | 10/1985 | Beiter | |
| 4,546,777 A | 10/1985 | Groch et al. | |
| 4,548,204 A | 10/1985 | Groch et al. | |
| 4,549,552 A | 10/1985 | Groch et al. | |
| 4,572,197 A | 2/1986 | Moore et al. | |
| 4,580,572 A | 4/1986 | Granek et al. | |
| 4,648,407 A | 3/1987 | Sackner | 128/721 |
| 4,672,975 A | 6/1987 | Sirota | |
| 4,753,088 A | 6/1988 | Harrison et al. | 525/73 |
| 4,777,962 A | 10/1988 | Watson et al. | 600/529 |
| 4,796,639 A | 1/1989 | Snow et al. | 600/532 |
| 4,800,495 A | 1/1989 | Smith | 364/413.03 |
| 4,807,640 A | 2/1989 | Watson et al. | 600/534 |
| 4,815,473 A | 3/1989 | Watson et al. | 600/534 |
| 4,817,625 A | 4/1989 | Miles | 128/721 |
| 4,819,752 A | 4/1989 | Zelin | |
| 4,834,109 A | 5/1989 | Watson | 600/534 |
| 4,860,766 A | 8/1989 | Sackner | 600/561 |
| 4,863,265 A | 9/1989 | Flower et al. | |
| 4,867,571 A | 9/1989 | Frick et al. | |
| 4,889,131 A | 12/1989 | Salem et al. | |
| 4,909,260 A | 3/1990 | Salem et al. | |
| 4,911,167 A | 3/1990 | Corenman et al. | |
| 4,920,969 A | 5/1990 | Suzuki et al. | |
| 4,928,692 A | 5/1990 | Goodman et al. | |
| 4,934,372 A | 6/1990 | Corenman et al. | |
| 4,955,379 A | 9/1990 | Hall | |
| 4,960,118 A | 10/1990 | Pennock | 128/200.24 |
| 4,966,155 A | 10/1990 | Jackson | 128/671 |
| 4,972,842 A | 11/1990 | Korten et al. | 600/529 |
| 4,981,139 A | 1/1991 | Pfohl | |
| 4,986,277 A | 1/1991 | Sackner | 600/485 |
| 5,007,427 A | 4/1991 | Suzuki et al. | 128/659 |
| 5,025,791 A | 6/1991 | Niwa | |
| 5,036,857 A | 8/1991 | Semmlow et al. | |
| 5,040,540 A | 8/1991 | Sackner | 600/485 |
| 5,074,129 A | 12/1991 | Matthew | 66/192 |
| 5,076,801 A | 12/1991 | Schroll | |
| 5,099,841 A | 3/1992 | Heinonen et al. | |
| 5,099,855 A | 3/1992 | Yount | |
| 5,111,817 A | 5/1992 | Clark et al. | |
| 5,111,818 A * | 5/1992 | Suzuki et al. | 600/390 |
| 5,131,399 A | 7/1992 | Sciarra | 600/484 |
| 5,143,089 A | 9/1992 | Alt | |
| 5,159,935 A | 11/1992 | Sackner et al. | 600/534 |
| 5,173,151 A | 12/1992 | Namose | |
| 5,178,151 A | 1/1993 | Sackner | 600/485 |
| 5,224,479 A | 7/1993 | Sekine | |
| 5,241,300 A | 8/1993 | Buschmann | |
| 5,271,551 A | 12/1993 | Roepke | 229/117.17 |
| 5,295,490 A | 3/1994 | Dodakian | |
| 5,299,120 A | 3/1994 | Kaestle | |
| 5,301,678 A | 4/1994 | Watson et al. | 600/534 |
| 5,329,932 A | 7/1994 | Yount | |
| 5,331,968 A | 7/1994 | Williams et al. | 600/534 |
| 5,333,106 A | 7/1994 | Lanpher et al. | |
| 5,348,008 A | 9/1994 | Bornn et al. | 600/301 |
| 5,353,793 A | 10/1994 | Bornn et al. | 600/386 |
| 5,416,961 A | 5/1995 | Vinay | 600/523 S |
| 5,447,164 A | 9/1995 | Shaya et al. | 128/710 |
| RE35,122 E | 12/1995 | Coreman et al. | 128/633 |
| 5,520,192 A | 5/1996 | Kitney et al. | |
| 5,533,511 A | 7/1996 | Kaspari et al. | 128/672 |
| 5,535,738 A | 7/1996 | Estes et al. | |
| 5,544,661 A | 8/1996 | Davies et al. | 128/700 |
| 5,564,429 A | 10/1996 | Bornn et al. | 128/696 |
| 5,577,510 A | 11/1996 | Chittum et al. | |
| 5,582,337 A | 12/1996 | McPherson et al. | 224/660 |
| 5,584,295 A | 12/1996 | Muller et al. | |
| 5,588,425 A | 12/1996 | Sackner et al. | 600/523 |
| 5,601,088 A | 2/1997 | Swanson et al. | 600/510 |
| 5,611,085 A | 3/1997 | Rasmussen | |
| 5,617,847 A | 4/1997 | Howe | |
| 5,694,939 A | 12/1997 | Cowlings | 600/484 |
| 5,718,234 A | 2/1998 | Warden et al. | |
| 5,719,950 A | 2/1998 | Osten et al. | |
| 5,720,709 A | 2/1998 | Schnall | |
| 5,724,025 A | 3/1998 | Tavori | |
| 5,749,365 A | 5/1998 | Magill | |
| 5,820,567 A | 10/1998 | Mackie | 600/519 |
| 5,825,293 A | 10/1998 | Ahmed et al. | |
| 5,848,027 A | 12/1998 | Dotter | |
| 5,882,307 A | 3/1999 | Wright et al. | |
| 5,899,855 A | 5/1999 | Brown | 600/301 |
| 5,913,830 A | 6/1999 | Miles | 600/535 |
| 5,921,920 A | 7/1999 | Marshall et al. | |
| 5,937,854 A | 8/1999 | Stenzler | |
| 5,989,193 A | 11/1999 | Sullivan | |
| 5,991,922 A | 11/1999 | Banks | 2/69 |
| 6,002,952 A | 12/1999 | Diab et al. | |
| 6,015,388 A | 1/2000 | Sackner et al. | 600/529 |
| 6,018,677 A | 1/2000 | Vidrine et al. | |
| 6,047,203 A | 4/2000 | Sackner et al. | 600/388 |
| 6,065,154 A | 5/2000 | Hulings et al. | 2/102 |
| 6,066,093 A | 5/2000 | Kelly et al. | 600/386 |
| 6,067,462 A | 5/2000 | Diab et al. | 600/310 |
| 6,068,568 A | 5/2000 | Kozakura et al. | 474/212 |
| 6,070,098 A | 5/2000 | Moore-Ede et al. | 600/544 |
| 6,120,441 A | 9/2000 | Griebel | |
| 6,142,953 A | 11/2000 | Burton et al. | 600/534 |
| 6,145,551 A | 11/2000 | Jayaraman et al. | |
| 6,179,786 B1 | 1/2001 | Young | |
| 6,198,394 B1 | 3/2001 | Jacobsen et al. | |
| 6,223,072 B1 | 4/2001 | Mika et al. | 600/510 |
| 6,254,551 B1 | 7/2001 | Varis | 600/595 |
| 6,261,238 B1 | 7/2001 | Gravely | 600/532 |
| 6,273,859 B1 | 8/2001 | Remmers et al. | |
| 6,287,264 B1 | 9/2001 | Hoffman | |
| 6,302,844 B1 | 10/2001 | Walker et al. | 600/300 |
| 6,306,088 B1 | 10/2001 | Krausman et al. | |
| 6,341,504 B1 | 1/2002 | Istook | 66/172 E |
| 6,361,501 B1 | 3/2002 | Amano et al. | |
| 6,381,482 B1 | 4/2002 | Jayaraman et al. | |
| 6,413,225 B1 | 7/2002 | Sackner et al. | 600/529 |
| 6,419,636 B1 | 7/2002 | Young et al. | |
| 6,436,057 B1 | 8/2002 | Goldsmith | 600/586 |
| 6,443,890 B1 | 9/2002 | Schulze et al. | |
| 6,449,504 B1 | 9/2002 | Conley et al. | 600/523 |
| 6,454,719 B1 | 9/2002 | Greenhut | |
| 6,461,307 B1 | 10/2002 | Kristbjarnarson et al. | |
| 6,463,385 B1 | 10/2002 | Fry | |
| 6,478,736 B1 | 11/2002 | Mault | |
| 6,483,929 B1 | 11/2002 | Murakami et al. | |
| 6,485,431 B1 | 11/2002 | Campbell | |
| 6,506,153 B1 | 1/2003 | Littek et al. | |
| 6,511,424 B1 | 1/2003 | Moore-Ede et al. | 600/300 |
| 6,513,532 B2 | 2/2003 | Mault et al. | |
| 6,551,252 B2 | 4/2003 | Sackner et al. | 600/536 |
| 6,579,231 B1 | 6/2003 | Phipps | 600/300 |
| 6,604,115 B1 | 8/2003 | Gary et al. | 707/104.1 |
| 6,633,772 B2 | 10/2003 | Ford et al. | 600/345 |
| 6,647,252 B2 | 11/2003 | Smith et al. | |
| 6,656,127 B1 | 12/2003 | Ben-Oren et al. | 600/532 |
| 6,687,523 B1 | 2/2004 | Jayaramen et al. | |
| 6,699,194 B1 | 3/2004 | Diab et al. | |
| 6,702,752 B2 | 3/2004 | Dekker | |
| 6,709,402 B2 | 3/2004 | Dekker | |
| 6,721,594 B2 | 4/2004 | Conley et al. | 600/523 |
| 6,723,055 B2 | 4/2004 | Hoffman et al. | 600/538 |
| 6,726,636 B2 | 4/2004 | Der Ghazarian et al. | |
| 6,727,197 B1 | 4/2004 | Wilson et al. | 442/301 |

(56) References Cited

U.S. PATENT DOCUMENTS

| | | | |
|---|---|---|---|
| 6,747,561 B1 | 6/2004 | Reeves | |
| 6,775,389 B2 | 8/2004 | Harrison et al. | |
| 6,783,498 B2 | 8/2004 | Sackner et al. | 600/481 |
| 6,801,916 B2 | 10/2004 | Roberge et al. | 707/101 |
| 6,817,979 B2 | 11/2004 | Nihtila | |
| 6,858,006 B2 | 2/2005 | MacCarter et al. | |
| 6,881,192 B1 | 4/2005 | Park | 600/529 |
| 6,941,775 B2 | 9/2005 | Sharma | |
| 6,961,448 B2 | 11/2005 | Nichols et al. | |
| 6,970,731 B1 | 11/2005 | Jayaramen et al. | |
| 6,993,378 B2 | 1/2006 | Wiederhold et al. | |
| 7,001,337 B2 | 2/2006 | Dekker | |
| 7,073,129 B1 | 7/2006 | Robarts et al. | |
| 7,077,810 B2 | 7/2006 | Lange et al. | |
| 7,081,095 B2 | 7/2006 | Lynn et al. | 600/538 |
| 7,082,327 B2 | 7/2006 | Houben | |
| 7,099,714 B2 | 8/2006 | Houben | |
| 7,104,962 B2 | 9/2006 | Lomask et al. | 600/529 |
| 7,154,398 B2 | 12/2006 | Chen et al. | |
| 7,207,948 B2 | 4/2007 | Coyle | |
| 7,254,516 B2 | 8/2007 | Case, Jr. et al. | |
| 7,267,652 B2 | 9/2007 | Coyle et al. | |
| 7,319,385 B2 | 1/2008 | Ruha | |
| 7,559,902 B2 | 7/2009 | Ting et al. | |
| 7,604,603 B2 | 10/2009 | Sackner et al. | |
| 7,670,295 B2 | 3/2010 | Sackner et al. | |
| 7,727,161 B2 | 6/2010 | Coyle et al. | |
| 7,762,953 B2 | 7/2010 | Derchak et al. | |
| 7,809,433 B2 | 10/2010 | Keenan | |
| 7,878,979 B2 | 2/2011 | Derchak | |
| 2002/0032386 A1* | 3/2002 | Sackner et al. | 600/536 |
| 2002/0084130 A1 | 7/2002 | Der Ghazarian et al. | |
| 2002/0090667 A1 | 7/2002 | Ratcliffe et al. | |
| 2002/0123701 A1 | 9/2002 | Eriksen et al. | |
| 2003/0100843 A1 | 5/2003 | Hoffman | |
| 2003/0135097 A1 | 7/2003 | Wiederhold et al. | |
| 2003/0135127 A1 | 7/2003 | Sackner et al. | 600/536 |
| 2003/0185408 A1 | 10/2003 | Causevic et al. | |
| 2003/0187341 A1 | 10/2003 | Sackner et al. | |
| 2004/0010420 A1 | 1/2004 | Rooks | |
| 2004/0019289 A1 | 1/2004 | Ross | |
| 2004/0030224 A1 | 2/2004 | Sotos et al. | |
| 2004/0073104 A1* | 4/2004 | Brun del Re et al. | 600/372 |
| 2004/0111040 A1 | 6/2004 | Ni et al. | 600/534 |
| 2004/0117204 A1 | 6/2004 | Mazar et al. | |
| 2004/0122334 A1 | 6/2004 | Yamashiro | |
| 2004/0143194 A1 | 7/2004 | Kihara et al. | 600/534 |
| 2004/0176674 A1* | 9/2004 | Nazeri | 600/382 |
| 2004/0204636 A1 | 10/2004 | Diab et al. | |
| 2004/0210147 A1 | 10/2004 | Houben | |
| 2004/0225227 A1 | 11/2004 | Newman | |
| 2004/0249299 A1 | 12/2004 | Cobb | 600/529 |
| 2005/0027207 A1 | 2/2005 | Westbrook et al. | |
| 2005/0054941 A1* | 3/2005 | Ting et al. | 600/529 |
| 2005/0076908 A1 | 4/2005 | Lee et al. | 128/204.23 |
| 2005/0119586 A1 | 6/2005 | Coyle et al. | 600/538 |
| 2005/0125970 A1 | 6/2005 | Nolan | 24/615 |
| 2005/0211247 A1 | 9/2005 | Noda et al. | |
| 2005/0228234 A1 | 10/2005 | Yang | 600/300 |
| 2005/0240087 A1 | 10/2005 | Keenan et al. | 600/301 |
| 2005/0256385 A1 | 11/2005 | Diab et al. | |
| 2006/0000420 A1 | 1/2006 | Davies et al. | |
| 2006/0036183 A1 | 2/2006 | Sackner et al. | 600/481 |
| 2006/0074334 A1 | 4/2006 | Coyle | |
| 2006/0122528 A1 | 6/2006 | Gal | |
| 2006/0178591 A1 | 8/2006 | Hempfling | 600/529 |
| 2006/0211934 A1* | 9/2006 | Hassonjee et al. | 600/372 |
| 2006/0258914 A1 | 11/2006 | Derchak et al. | |
| 2006/0293609 A1 | 12/2006 | Stahmann et al. | |
| 2007/0027368 A1 | 2/2007 | Collins et al. | |
| 2007/0049843 A1 | 3/2007 | Derchak | |
| 2007/0050715 A1 | 3/2007 | Behar | |
| 2007/0100622 A1 | 5/2007 | Tavares | |
| 2007/0150006 A1 | 6/2007 | Libbus et al. | |
| 2007/0177770 A1 | 8/2007 | Derchak et al. | |
| 2007/0208262 A1 | 9/2007 | Kovacs | |
| 2007/0209669 A1 | 9/2007 | Derchak | |
| 2007/0270671 A1 | 11/2007 | Gal | |
| 2008/0015454 A1 | 1/2008 | Gal | |
| 2008/0027341 A1 | 1/2008 | Sackner et al. | |
| 2008/0045815 A1 | 2/2008 | Derchak et al. | |
| 2008/0051839 A1 | 2/2008 | Libbus et al. | |
| 2008/0082018 A1 | 4/2008 | Sackner et al. | |
| 2008/0221401 A1 | 9/2008 | Derchak et al. | |
| 2008/0269644 A1 | 10/2008 | Ray | |
| 2009/0131759 A1 | 5/2009 | Sims et al. | |
| 2010/0274100 A1 | 10/2010 | Behar et al. | |
| 2011/0009766 A1 | 1/2011 | McCool | |

FOREIGN PATENT DOCUMENTS

| | | |
|---|---|---|
| EP | 0875199 A1 | 4/1998 |
| GB | 1596298 A | 8/1981 |
| GB | 2116725 | 9/1983 |
| JP | 53126786 A | 6/1978 |
| JP | 58109031 A | 6/1983 |
| JP | 6337933 A | 2/1988 |
| JP | 1091834 | 4/1989 |
| JP | 5168602 | 7/1993 |
| JP | 5298589 | 11/1993 |
| JP | 7227383 A | 8/1995 |
| JP | 2001516253 A | 9/1998 |
| JP | 2001104259 A | 4/2001 |
| WO | WO9810699 | 3/1998 |
| WO | WO 0128420 | 4/2001 |
| WO | WO 01/76467 A2 | 10/2001 |
| WO | WO 02/060370 A2 | 8/2002 |
| WO | WO02069878 | 12/2002 |
| WO | WO03022149 | 3/2003 |
| WO | WO 2004019503 | 3/2004 |
| WO | WO 2005/115242 A2 | 12/2005 |
| WO | WO 2006/009830 A2 | 1/2006 |
| WO | WO 2006002338 | 1/2006 |
| WO | WO 2007021645 | 2/2007 |
| WO | WO 2007/069111 A2 | 6/2007 |
| WO | WO 2007089751 | 8/2007 |
| WO | WO 2009/074973 A1 | 6/2009 |
| WO | WO2010027515 | 11/2010 |

OTHER PUBLICATIONS

International Search Report and Written Opinion of the International Searching Authority, application No. PCT/US06/60264, dated Jan. 15, 2008.

6th Portuguese Conference on Biomedical Engineering,"BioEng' 2001 Conference Papers", (Jun. 2001) 6 pages.

Aliverti. et al., "Chronic Obstructive Pulmonary Disease: Regional Chest Wall Volumes During Exercise in Chronic Obstructive Pulmonary Disease." *Thorax*, 59:210-216, 7 pages, 2004.

Almeida et al., "Wavelet Transform Based Matlab System for the Detection and Delineation of QRS Complexes in Ambulatory ECG Recordingd", *6th Portuguese Conference on Biomedical Engineering* (Jun. 2001), 2 pages.

Anderer et al.,"Artifact Processing in Computerized Analysis of Sleep EEG—A Review" *Neuropsychobiology*, 40:150-157 (1999), 8 pages.

Bianchi et al., "Extraction of the Respiration Influence From the Heart Rate Variability Signal by Means of Lattice Adaptive Filter", *IEEE Transactions on Biomedical Engineering*, pp. 121-122 (1994), 2 pages.

National Biometric Test Center, "The Functions of Biometric Identification Devices", *San Jose State University Biometrics Publications*, www.engr.sjsu.edu/biometrics/publications_tech.html (printed Jul. 28, 2005), 25 pages.

National Biometric Test Center, "Biometric Technology—Testing, Evaluation, Results", *San Jose State University Biometrics Publications*, www.engr.sjsu.edu/biometries/publications_tech.html (printed Jul. 28, 2005), 13 pages.

Blechert et al., "Identifying Anxiety States Using Broad Sampling and Advance Processing of Peripheral Physiological Information," *Psychosom Med Dec. 2007*; 69(9):935-43 Epub Nov. 8, 2007, 6 pages.

(56) References Cited

OTHER PUBLICATIONS

Bloch et al., "Specific respiratory patterns distinguish among human basic emotions," *International Journal of Psychophysiology*, 11:141-154 (1991), 14 pages.
Bonnet et al., "EEG Arousals: Scoring Rules and Examples, A Preliminary Report from the Sleep Disorders Atlas Task Force of the American Sleep Disorders Association," *Sleep*, 152(2): 173-184 (1992), 12 pages.
Brack, "Cheyne-Stokes respiration in patients with congestive heart failure," *Swiss Med Weekly* 133:605-610 (2003), 7 pages.
Costa et al., "Multiscale Entropy Analysis of Complex Physiologic Time Series," *Physical Review Letters* 89(6):068102-1-4 Aug. 5, 2002, 4 pages.
Coyle et al., "Home Measurement of Cough Indicates Circadian Frequency Pattern and Abnormal Distribution During Sleep," *LifeShirt System*, study sponsored by Pfizer, Inc., Jun. 2004, 1 page.
Gore Electronic Products, "Expanded PTFE Insulation Material", www.goreelectronics.com (visited Aug. 2005), 4 pages.
Grossman et al., "Reliability of Respiratory Tidal Volume Estimation by Means of Ambulatory Inductive Plethysmography," *Biomed Sci Instrum* 42:193-8 (2006), 6 pages.
Grossman et al., "A Comparison of Three Quantification Methods for Estimation of Respiratory Sinus Arrhythmia", *Psychophycology*, 27(6):702-714 (1990), 17 pages.
Istepanian et al., "Microcontroller-Based Underwater Acoustic ECG Telemetry System", *IEEE Transactions on Information Technology in Biomedicine*, 1(2):150-154 (Jun. 1997), 5 pages.
Keenan et al., "Adaptive Filtering of Heart Rate Signals for an Improved Measure of Sympathovagal Balance," Jan. 1, 2005, 8 pages.
Klabunde, "Electrocardiogram (EKG, ECG)", Cardiovascular Physiology Concepts, www.cvphysiology.com (visited Mar. 2005), 3 pages.
Lake et al., "Sample entropy analysis of neonatal heart rate variability," *Am J Physiol Regul Integr Comp* 283:R789-97 (2002), 10 pages.
Marin et al., "Inspiratory Capacity, Dynamic Hyperinflation, Breathlessness, and Exercise Performance During the 6-Minute-Walk Test in Chronic Obstructive Pulmonary Disease", *Am. J. Respir. Crit. Care Med.*, vol. 163., pp. 1395-1399, (2001), 5 pages.
McCool et al., "Estimates of ventilation from body surface measurements in unstricted subjects," *Appl. Physiol.* 61(3):1114-9 (1986), 6 pages.
McCool et al., "Tidal Volume and Respiratory Timing Derived From a Portable Ventilation Monitor," *Chest* 122:684-91 (2002), 10 pages.
McNaughton et al., "Metallized Polymer Fibers As Leadwires and Intrafascicular Microelectrodes", *J. Neurosci. Methods*, 70(1):103-10 (1996), 2 pages.
Micro-Coax, "About Micro-Coax", www.micro-coax.com (visited Aug. 2004), 9 pages.
Niskanen et al., "Software for Advanced HRV Analysis", *University of Kuopio Department of Applied Physics Report Series*, pp. 1-11 (Feb. 2002), 12 pages.
O'Donnell, "Ventilatory Limitations in Chronic Obstructive Pulmonary Disease", *Medicine & Science in Sports & Exercise*, pp. S647-S655, (2001), 9 pages.
O'Donnell et al., "Dynamic Hyperinflation and Exercise Intolerance in Chronic Obstructive Pulmonary Disease", *Am. J. Respir. Crit. Care Med.*, 164:770-777 (2001), 8 pages.
Park et al., "Automated Detection and Elimination of Periodic ECG Artifacts in EEG Using the Energy Interval Histogram Method", *IEEE Transactions on Biomedical Engineering* 49(12):1526-1533 (2002), 8 pages.
Pietraszek et al., "Simple Telemetry System for ECG Recording", *Polish J. Med. Phys. & Eng.* 2002; 8(3): 193-198, 4 pages.
Rampil, "A Primer for EEG Signal Processing in Anesthesia," *Anesthesiology* 89(4):980-1002 Oct. 1998, 15 pages.
Richman et al., "Physiological time-series analysis using approximate entropy and sample entropy," *Am J. Physiol Circ Physiol* 278:H2039-49 (2000), 11 pages.
Signal Consulting Inc., "Inductance of Circular Loop", www.sigcon.com (visited Aug. 2005), 2 pages.
Sijbers et al., "Reduction of ECG and gradient related arifacts in simultaneously recorded human EEG/MRI data," *Magnetic Resonance Imaging* 18:881-6 (2000), 6 pages.
Snyder et al., "Ventilatory Responses to Hypoxia and High Altitude During Sleep in Aconcagua Climbers," *Wilderness and Environmental Medicine* 18:138-145 (2007), 8 pages.
Szabo et al., "Prognostic Value of Heart Rate Variability in Chronic Congestive Heart Failure Secondary to Idiopathic or Ischemic Dilated Cardiomypathy," *Am J Cardiol.* 79:978-980 (1997), 3 pages.
van Dijk et al., "Determinants of Brachial Artery mean 24 h PulsePressure in Individuals with Type II diabetes mellitus and untreated mild hypertension", *Clinical Science* (2002), 102, pp. 177-186, 10 pages.
Vogiatzis, et al., "Respiratory Kinematics by Optoelectronic Plethysmography During Exercise in Men and Women.", *Eur J of App Physiol*, 581-587, 7 pages, 2004, 7 pages.
Wilhelm et al., "Distinguishing Emotional From Physical Activation in Ambulatory Psychophysiological Monitoring," *Biomed Sei Instrum* 42:458-63 (2006), 6 pages.
Wilhelm et al., "Taking the laboratory to the skies: Ambulatory assessment of self-report, autonomic, and respiratory responses in flying phobia," *Psychophysiology* 35:596-606 (1998), 11 pages.
Supplementary Partial European Search Report of the European Patent Office, Application No. EP 06784447.2, dated Jan. 20, 2010, 9 pages.
International Search Report and the Written Opinion of the International Searching Authority, application No. PCT/US2008/061171, dated Nov. 14, 2008, 10 pages.
International Search Report and the Written Opinion of the International Searching Authority, application No. PCT/US06/60264, dated Jan. 15, 2008, 8 pages.
International Search Report and the Written Opinion of the International Searching Authority, application No. PCT/US2007/82688, dated May 8, 2008, 7 pages.
International Search Report and the Written Opinion of the International Searching Authority, application No. PCT/US2008/072414, dated Nov. 12, 2008, 7 pages.
Extended European Search Report for Application No. EP 07798146.2, Applicant: adidas AG, mailed Oct. 19, 2010.
U.S. Appl. No. 11/357,772, Sackner, System and Methods for Ambulatory Monitoring of Physiological Signs, filed Feb. 17, 2006.
U.S. Appl, No. 11/373,822, Sackner, System and Methods for Ambulatory Monitoring of Physiological Signs, filed Mar. 9, 2006.
U.S. Appl. No. 12/231,692, McCool, Noninvasive Method and System for Measuring Pulmonary Ventilation, filed Sep. 5, 2008.
U.S. Appl. No. 12/869,576, Stone, Method and System for Limiting Interference in Magnetometer Fields, filed Aug. 26, 2010.
U.S. Appl. No. 12/869,578, Derchak, Noninvasive Method and System for Monitoring Physiological Characteristics, filed Aug. 26, 2010.
U.S. Appl. No. 12/869,582, Derchak, Noninvasive Method and System for Monitoring Physiological Characteristics and Athletic Performance, filed Aug. 26, 2010.
U.S. Appl. No. 12/869,585, Derchak, Noninvasive Method and System for Monitoring Physiological Characteristics and Athletic Performance, filed Aug. 26, 2010.
U.S. Appl. No. 12/869,586, Derchak, Physiological Database and System for Population Modeling and Method of Population Modeling, filed Aug. 26, 2010.
U.S. Appl. No. 12/869,592, Derchak, Multimodal Method and System for Transmitting Information About a Subject, filed Aug. 26, 2010.
U.S. Appl. No. 12/869,625, Derchak, Method and System for Interpretation and Analysis of Physiological, Performance, and Contextual Information, filed Aug. 26, 2010.
U.S. Appl. No. 12/869,627, Derchak, Physiological Monitoring Garment, filed Aug. 26, 2010.

(56) References Cited

OTHER PUBLICATIONS

U.S. Appl. No. 12/872,174, Derchak, Physiological Monitoring Garment, filed Aug. 31, 2010.
Office Action dated Aug. 2, 2010 from U.S. Appl. No. 11/373,822, Sacluier, System and Methods for Ambulatory Monitoring of Physiological Signs, filed Mar. 9, 2006.
Office Action dated Sep. 28, 2010 from U.S. Appl. No. 11/503,350, Behar, Systems and Methods for Monitoring Subjects in Potential Physiological Distress, Aug. 10, 2006.
Office Action dated Oct. 15, 2010 from U.S. Appl. No. 11/627,198, Derchak, System and Method for Identity Confirmation Using Physiologic Biometrics to Determine a Physiologic Fingerprint, filed Jan. 25, 2007.
Supplementary Partial European Search Report of the European Patent Office, Application No. EP 04759405.6, dated Jan. 24, 2011, 4 pages.
Office Action dated Nov. 30, 2010 from Japanese Appl. No. 2006-509897, Adidas AG, Systems and Methods for Respiratory Event Detection, with translation.
Wachowski, Andy and Larry, The Matrix, released Mar. 31, 1999 by Warner Bros. Pictures, see 1:26:29, 2:03:10, and 2:04:41, 13 pages.
Extended European Search Report for Application No. EP 10174873.9, Applicant: adidas AG, mailed Dec. 8, 2010.
Extended European Search Report for Application No. EP 10174680.8, Applicant: adidas AG, mailed Dec. 9, 2010.
Extended European Search Report for Application No. EP 10174876.2, Applicant: adidas AG, mailed Dec. 9, 2010.
Extended European Search Report for Application No. EP 10174881.2, Applicant: adidas AG, mailed Dec. 9, 2010.
Extended European Search Report for Application No. EP 10174683.2, Applicant: adidas AG, mailed Dec. 27, 2010.
Partial European Search Report for Application No. EP 10174885.3, Applicant: adidas AG, mailed Jan. 4, 2011.
Office Action dated Nov. 18, 2010 from U.S. Appl. No. 11/492,484, Behar, Computer Interfaces Including Physiologically Guided Avatars, filed Jul. 24, 2006.
Office Action dated Jan. 4, 2011 from U.S. Appl. No. 11/233,317,Gal, Improved Sensors for Inductive Plethysmographic Monitoring Applications and Apparel Using Same, Sep. 21, 2005.
Office Action dated Jan. 27, 2011 from U.S. Appl. No. 10/991,877, Keenan, Method and system for processing data from ambulatory physiological monitoring, Nov. 18, 2004.
Office Action dated Feb. 2, 2011 from U.S. Appl. No. 11/373,822, Sackner, Systems and methods for ambulatory monitoring of physiological signs, Mar. 9, 2006.
U.S. Appl. No. 12/971,193, Sackner, Systems and Methods for Ambulatory Monitoring of Physiological Signs, filed Dec. 17, 2010.
U.S. Appl. No. 12/976,080, Derchak, Methods and Systems for Monitoring Respiratory Data, filed Dec. 22, 2010.

\* cited by examiner

BAND-LIKE GARMENT FOR PHYSIOLOGICAL MONITORING

CROSS REFERENCE TO RELATED APPLICATIONS

This application is a continuation of U.S. provisional application No. 60/730,890 filed Oct. 26, 2005 and a continuation-in-part of U.S. patent application Ser. No. 11/233,317, now U.S. Pat. No. 8,034,901, filed Sep. 21, 2005. These patents and applications are incorporated by reference herein in their entireties.

FIELD OF THE INVENTION

This application relates to ambulatory physiological monitoring, and particularly to garments for ambulatory physiological monitoring that provide or incorporate a plurality of physiological sensors.

BACKGROUND OF THE INVENTION

Ambulatory physiological monitoring has many applications in sports, medicine, industry and the military. In all these applications, it is advantageous to configure sensors on an comfortable, unobtrusive garment to be worn by a monitored individual.

Among the known technologies for physiological monitoring is inductive plethysmography ("IP"). IP applied to respiratory monitoring, respiratory IP ("RIP"), has been shown to be a reliable and robust monitoring technology. RIP devices and processing methods are described in U.S. patents and US patent applications including: U.S. Pat. No. 6,047,203 issued Apr. 4, 2000; U.S. Pat. No. 6,551,252 issued Apr. 22, 2002; and Ser. No. 10/822,260 filed Apr. 9, 2004. These patents are included by reference herein in their entireties for all purposes.

Known physiological monitoring garments have been configured in the form of clothing for significant portions of a subject's body, such as shirts, pants, and the like. Known clothing items of such type are not advantageous in certain applications of physiological monitoring, for example, in situations where strenuous activity is possible or when personal garment size fitting is not possible.

SUMMARY OF THE INVENTION

Objects of this invention include providing physiological monitoring garments that are suitable for subjects that can engage in strenuous exertion. The garments of this invention cover only limited sections of a subject's body, and further are easy to use, add little weight, are easy to don and remove.

The garments of this invention are preferably configured as bands or straps that encircle portions of an individuals torso, e.g., a portion of the chest, and carry or incorporate sensors for physiological monitoring tasks such as monitoring respiration, heart rate, and the like. Preferred garments have integrated ECG electrodes and incorporate RIP ("respiratory inductive plethysmographic") sensors. Sensors are optionally arranged into an active section of the garment.

The band-like garments of this invention preferably include one (optionally more than one) straps, e.g., over-the-shoulder straps, that provides increased stability on a wearer. Associated electronics modules for, e.g., sensor signal processing and telemetry, are preferably mechanically isolated from the band-like garments to further improve garment stability. These modules can be carried on other items of clothing, e.g., a belt.

Band-like or strap-like garments of this invention can readily by configured for a subject and/or accommodate a subject of a range of body sizes, body shapes, and body types. Preferably, a garment has an adjustment portion linked to a single-size active portion. The adjustment portion serves to adapt the single-sized active portion to particular wearers so that is fits snugly about a subject. A garment also preferably includes one or more over-the-shoulder straps; the straps are linked to the band with buckles that permit free angular motion and allow lateral adjustment along the band.

Band-like or strap-like garments of this invention have a simple, easily made, and economical construction. In a preferred embodiment, a band is constructed from a length of fabric material that is folded and arranged so as to serve as a backbone which protects sensors within pockets or folds or carries sensors attached to exterior surfaces RIP is the preferred technology for sensing respiratory function. A garment can directly incorporate RIP sensor conductors into the materials of which it is constructed or can support a material in which these conductors are incorporated. RIP sensors are generally band-like materials extending throughout substantially all the active section of a band and preferably carry RIP sensor conductors and supplementary conductors that can serve as leads for additional sensors. (Other similarly lengthwise extended sensors can also include supplementary conductors to use as leads.) A preferred RIP sensor is described in U.S. patent application Ser. No. 11/233,317, filed Sep. 21, 2005. Alternatively, other length sensitive respiratory sensors can be used along with or in place of RIP sensors.

A band preferably includes sensors for at least one-lead of ECG signals. ECG sensor can be conductive electrodes in direct contact with the subject that have such physical, conductive and moisture handling properties so as to obtain sufficient electrical contact occurs without the use of special conductive gels and the like and to be comfortable and unobtrusive to the subject. Preferred electrodes use conductive cloth-like material optionally mounted on an pillow of elastic foam-like material. Other sensors can include: alternative cardiac sensors: thermistors for measuring skin temperature; microphones in contact with the wearer for responding to sounds generated in the wearer's body; accelerometers for measuring position and activity.

Further aspects and details and alternate combinations of the elements of this invention will be apparent from the following detailed description and are also within the scope of the inventor's invention.

BRIEF DESCRIPTION OF THE DRAWINGS

The present invention may be understood more fully by reference to the following detailed description of the preferred embodiment of the present invention, illustrative examples of specific embodiments of the invention and the appended figures in which.

DETAIL DESCRIPTION OF THE PREFERRED EMBODIMENTS

References to elements in the figures are identified by numerals and by abbreviations, e.g., "ADJ". Numerals and abbreviations are used consistently throughout the figures; only their first use is specifically identified.

Figure 1A:
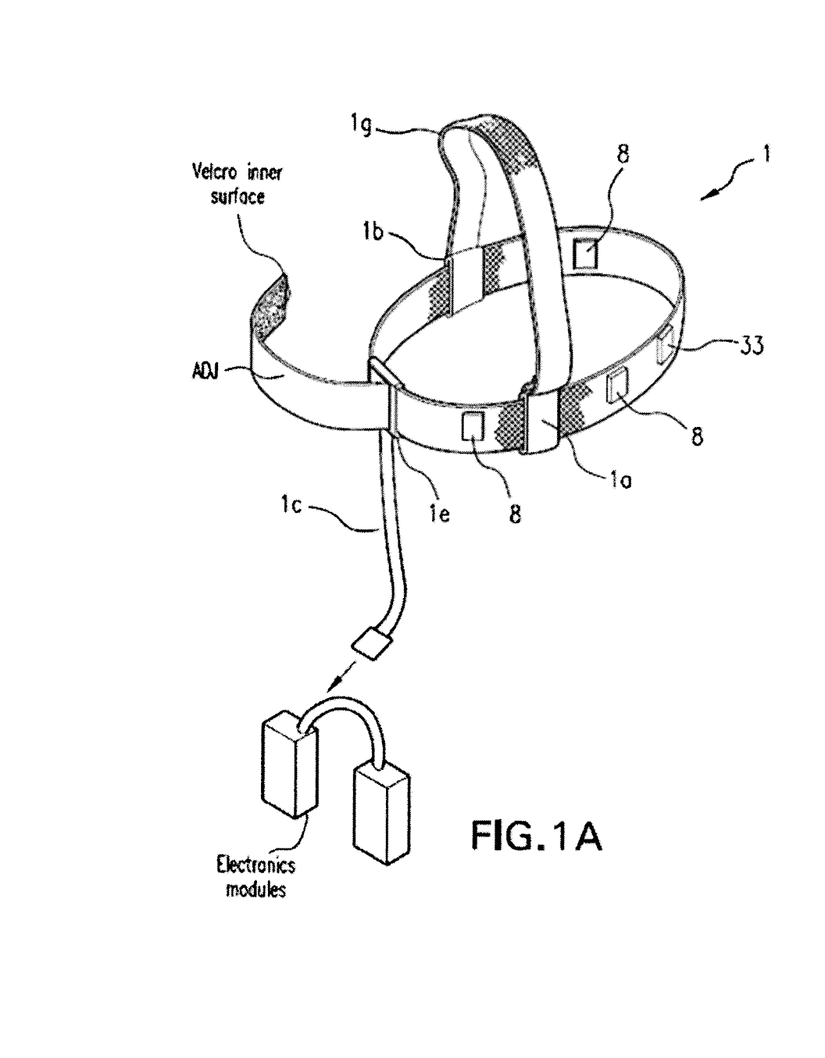
FIG. 1A-B illustrates preferred band-like garments of this invention.

FIG. 1A generally illustrates an angled view of an example of a preferred embodiment of a band-like (or a strap-like) physiological monitoring garment 1 of this invention (also referred to herein as a "HRT" strap). The garment comprises a flexible band of limited width and of sufficient length to encircle the torso of a monitored subject. It includes at least one adjustment section ("ADJ") and one or more active sections ("ACT"). The active sections provide for one or more physiological sensors that can be carried on the band, or can be integral to the band, or can be directly incorporated into the fabrics and other materials of the band. For example, sensors can be carried on a band in pockets, or fastened to a surface (e.g., by sewing, by adhesive, by snaps, by Velcro® strips, and so forth), or otherwise supported by a band. Sensors can be directly incorporated into active portions of a band by weaving, knitting, crocheting, or the like into the fabrics used in these portions, or by being within polymer structures that are integral to the active portions, or by other means.

In the band of FIG. 1A, that active sections, which are largely within the left-half of the band, include two active ECG electrodes 8 and one ECG ground electrode 8 (and/or third party cardiac sensors); one or more skin temperature sensors 33; and respiratory sensors. The ECG electrodes illustrated are mounted on the inner surface (that is the surface facing inward toward the subject) of the band by, e.g., sewing, or adhesive, or the like, so that they are in direct contact with the subject's skin. In preferred embodiments, they include flexible, conductive portions (e.g., a conductive cloth), and can be vertically ("VERT") mounted (e.g., perpendicular to the long axis of the band), or horizontally ("HORIZ") mounted (e.g., parallel to the long axis of the band), or at another orientation. Here, ECG sensing electrodes are vertical while ECG ground ("GND") electrodes are horizontal. In preferred embodiments, the respiratory sensors are directly incorporated into the materials of the band and so are not readily visible in FIG. 1A. Other band embodiments can provide for additional sensors or for different sensors.

Sensor signals are received and processed, e.g., digitized and filtered, by associated electronic circuitry, that, in preferred embodiments, is carried by the monitored subject by being, e.g., carried on the band itself, or carried on another garment worn concurrently with the band, such as in a pouch or pocket of a shirt, or clipped to a belt, or the like. A preferred embodiment of such electronic circuitry is described in U.S. provisional patent application 60/791,005 filed Apr. 10, 2006. Thereby, the present invention can be part of a complete ambulatory physiological monitoring system. FIG. 1A illustrates two such electronics modules which are coupled to the sensors of the associated band by a flexible ribbon cable 1c with a cloth support and connector (model HR30-10/12), and which are also coupled to each other. Alternatively, sensors and electronic circuitry can be coupled by other varieties of cables, or by a personal wireless link in LAN, or the like. For example, the first module can perform sensor signal processing, and the second module can record or transmit processed data. Alternatively, these and other functions may be housed in a single physical module. Preferred housings and arrangements of associated electronics generally depends on the intended uses of this monitoring garment, e.g., in military applications, in clinical applications, in ambulatory applications, in athletic applications, and the like.

The ADJ section of the band of FIG. 1A, which is largely within the left-half of the band and is illustrated in an open configuration, comprises mating Velcro® surfaces that can hold the band at variable lengths so that it can be donned by a subject at a tension sufficient to prevent or limit motion of the band during expected subject activities (in various embodiments, from rest to vigorous activity). One surface threads through buckle 1e and then folds back. Alternatively, buckles, snaps, ties, and the like, can be used to adjust band length; also, the ADJ sections (or the entire band) can be elastic so that sufficient tension is achieved without the need for adjustment devices. An optional over-the-shoulder strap 1g extends from an anterior front buckle ("FB") 1a affixed to the band, over a subject's shoulder, and to a posterior rear buckle ("RB") 1b affixed to the band, serves to further prevent or limit band motion during expected activities.

Figure 1B:
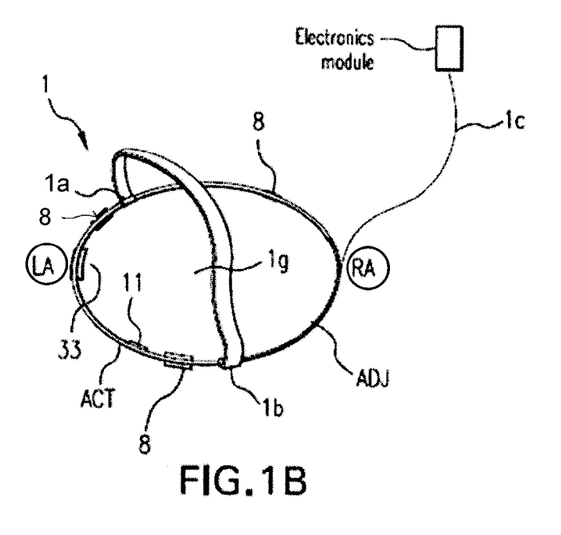

FIG. 1B provides another illustration of the configuration and construction of the exemplary band 1 of FIG. 1A. This figure illustrates how the band-like garment is worn about the chest of a monitored subject, were the resting position of the subject's left arm ("LA") and right arm ("RA") are indicated for reference. The mating Velcro® strips of the ADJ section is closed so that the band is held snugly about the chest by the tension adjustment section (ADJ). The band is further stabilized by the over-the-shoulder strap 1g that extends over the subject's left should from the FB 1a to the RB 1b. ECG sensor electrodes 8 are positioned anterior on the band's inner surface to contract the left and right anterior chest, and an ECG ground electrode is positioned posterior also on the bands inner surface. The active section of the band contacts the posterior, the left lateral, and the anterior chest and includes a schematically-illustrated respiratory inductive plethysmographic ("RIP") sensor 11 that is incorporated into the posterior, the left lateral, and the anterior sections of the band. Skin temperature sensor 33 is mounted on the band's left lateral inner surface. Conductors 1c to an external electronics module connect to the band at one end of the adjustment section (indicated by "A").

Figure 2:
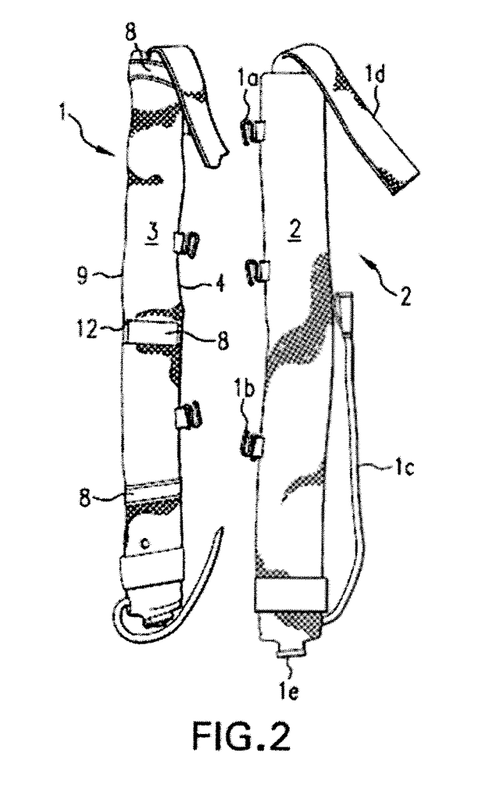
FIG. 2 illustrates an example of a preferred band-like garment.

FIG. 2 illustrates a outer-surface and an inner-surface of a lengthwise-extended, example of a preferred band 1 of this invention, which affords further appreciation of the configuration and construction of the preferred embodiments of this invention. The inner surface 3 of this embodiment carries three ECG electrodes 8, two of which are ECG sensors, the third being an ECG ground. Also visible are outer surface 2 with FB 1a and RB 1b. This band also incorporates a RIP sensor band (not visible) that is 26 in. long in a relaxed condition. The adjustment section here includes a strip of webbing 1d which can be fixed at various lengths through buckle 1e. Other methods of connection of the webbing and the band, such as plastic snap connectors, are also suitable. Alternatively, the webbing can include an elastic section that is permanently fixed to both ends of the bands' active section. A connection from the band's sensors to external circuitry, such as electronic modules, is provided here by thin, rope-like cable 1c linked to a plug-like connector. Alternatively and as illustrated in FIG. 1A, this connection can be provided by a ribbon-like cable, preferably an flexible cloth-backed ribbon cable. Folds at 4 and 9 are discussed with respect to FIG. 3A.

Figure 3A:
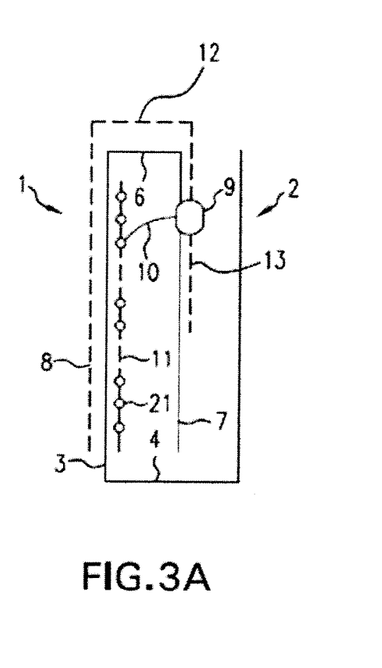
FIG. 3A-C illustrate further details of a band-like garment and of a preferred embodiment of an ECG electrode.
Figure 3B:
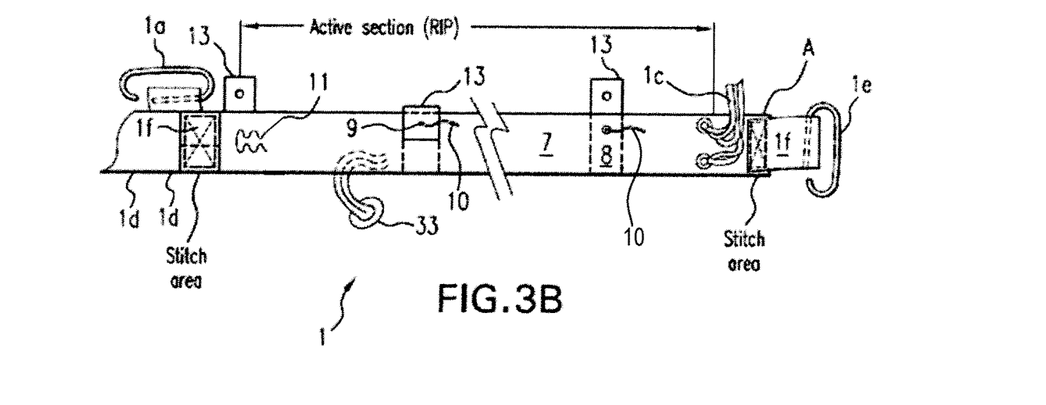
Figure 3C:
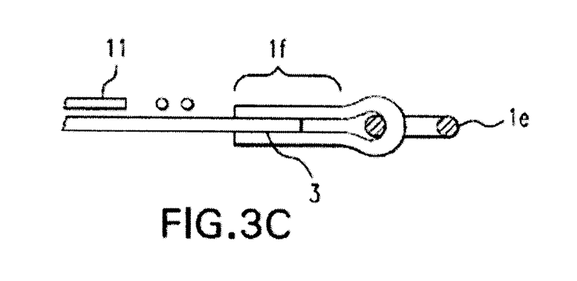

FIGS. 3A-C illustrate further details of one preferred embodiment of the band-like garments of this invention. FIG. 3A illustrates a transverse cross section through an active section of a preferred band, such as the band illustrated in FIGS. 1A-B and 2, at the position of a vertically-mounted flexible ECG electrode, e.g., the electrode adjacent to reference numeral 12. The backbone of a band of this embodiment is an elongated length of flexible, preferably fabric, material that is twice folded back onto itself along the longitudinal axis. Backbone material is represented in FIG. 3A by the thick, solid, black line. Tracing along the backbone folding pattern in detail, the backbone material first forms outer surface 2, then is folded back onto itself along longitudinal axis 4, then forms inner surface 3, then is folded back onto itself again along longitudinal axis 6, and then finally forms inner flap 7 positioned between inner face 3 and outer face 2. ECG electrode 8 is folded along with the supporting material. RIP sensor 11 is further described later. The backbone material preferably has a comfortable feel, is breathable, is washable, is resistant to sweat and skin microorganisms, has properties suitable for continuous use in vigorous activity, including and so forth. The backbone material is optionally elastic. Nylon fabric is a generally suitable backbone material, Polartech, or Underarmour, or similar fabrics, are more preferred.

FIG. 3B illustrates a view of inner flap 7 of an active portion and of an adjacent adjustment portion. Portions of three ECG electrodes 8 are illustrated: "ECG1", "ECG2" and "ECG-GND". FIGS. 3A and 3B together make clear that the flexible ECG electrode materials are affixed to inner surface 3, are folded back at axis 12, and continue and are affixed to inner flap 7. Electrical contact with the ECG electrodes is then made by button-like conductive elements 9 (preferably of a type known as "mini-anorak") which are affixed to electrode tabs 13 and which anchor conductive leads 10. This construction has the advantage that the only exposed portion of the ECG electrode material faces and is in contact with the subject; the remaining portions of the electrode material, the connecting buttons, and the electrical leads are in a recess between inner flap 7 and outer surface 2 and so are protected from external damage.

A portion of flap 7 is cutaway at the left of FIG. 3B so that RIP sensor 11 is apparent between the inner surface fabric 3 and the flap fabric 7 (see also FIG. 3C). A RIP sensor must contract and expand with the subject's respiratory and cardiac movements, and must therefore be able to accommodate relative length changes, preferably, up to approximately 20-40% (or 5-10 in. for a band of 30 in. rest length). Accordingly, the RIP sensor is preferably elastic, for example, incorporating Spandex, Lycra®, elastane, or other elastic filaments into a fabric backbone, and is mounted on the backbone material so length changes are not restricted. Alternately, the backbone fabric is also elastic and contract and expand along with an incorporated RIP sensor.

The illustrated band also carries skin temperature sensor 33. Sensor 33 along with its connecting leads are illustrated here, for clarity only, as being held away from the band-like garment; normally sensor 33 is carried on the inner surface of the band. Bands can also include additional sensors. For example, third party cardiac sensors (e.g., from Polar, Inc.) provide heart rate information, by producing electromagnetic bursts upon detecting heart beats which can be inductively received by a wire pick-up coil. Illustrated here are connectors for carrying such a third party sensor on the band.

This illustrated band is donned by a subject and fit snugly by pulling a tongue of webbing, 1d in FIGS. 2 and 3B, through (and back through) buckle 1e. Other connectors can be used in place of buckle 1e. An end of an optional over-the-shoulder strap can be fixed at front buckle 1a.

FIG. 3C illustrates a preferred attachment of buckles, loops, and similar fixtures to a band-like garment. A short length of attachment material, such as webbing material, is threaded through the loop, folded over a portion of a band, and then both ends of the attachment material are sewn through the band material region 1f. FIG. 3C illustrates loop 1e attached to both surfaces 2 and 3 of backbone material by webbing sewn through the band in region 1f; RIP sensor 11 is adjacent to this attachment.

Figure 4A:
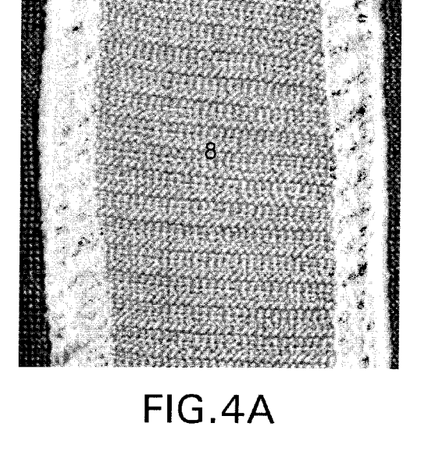
FIG. 4A-B illustrate views of an example of a preferred conductive fabric suitable for ECG electrode.
Figure 4B:
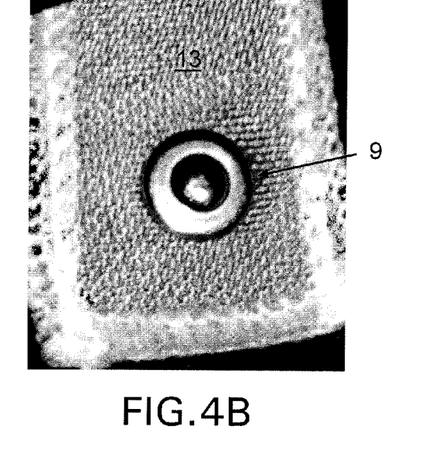
Figure 5A:
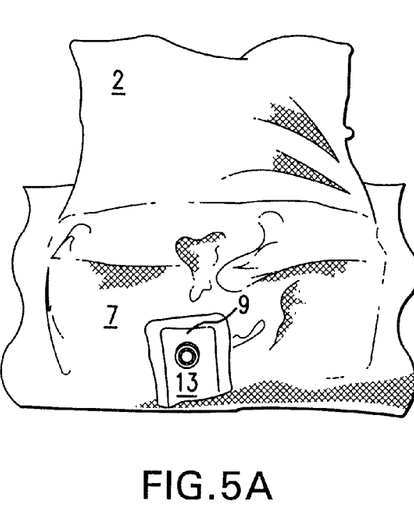
FIG. 5A-B illustrate details of an example of a preferred ECG electrode.
Figure 5B:
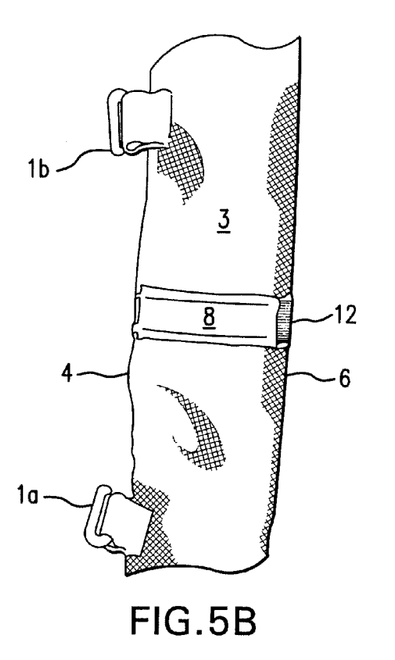
Figure 6A:
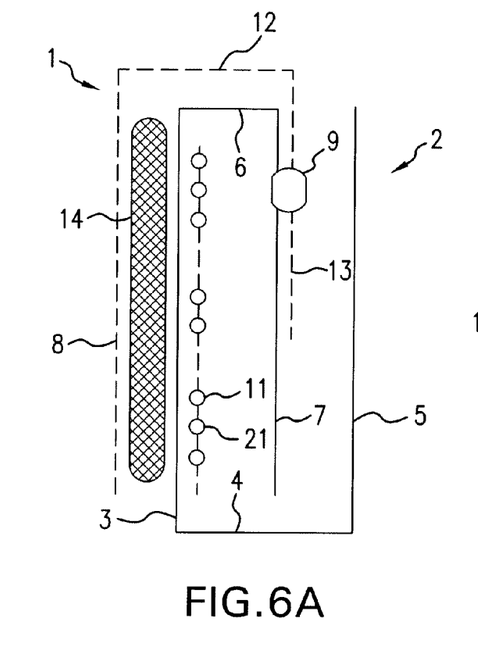
FIG. 6A-B illustrate another preferred embodiment of an ECG electrode.
Figure 6B:
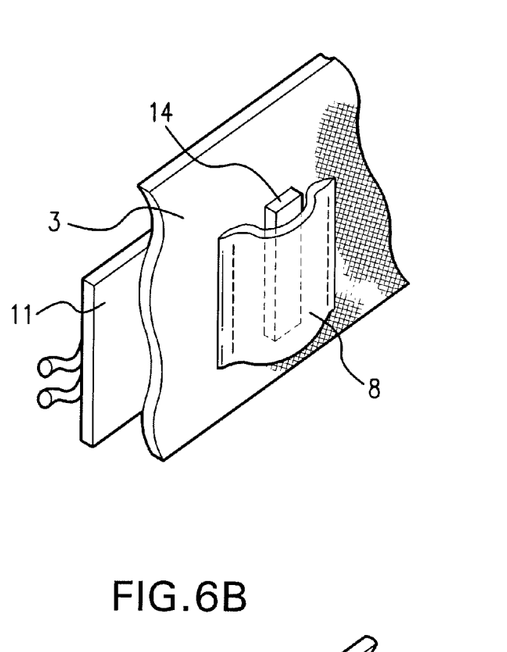

Preferred ECG electrodes are now described in view of FIG. 3A, which illustrates one preferred electrode embodiment; FIGS. 4A-B, which illustrate a preferred, flexible electrode material; FIGS. 5A-B, which illustrate an example of this first embodiment; FIGS. 6A-B, which illustrate a second preferred electrode embodiment; and FIGS. 7A-B, which illustrate a further preferred electrode embodiment.

The preferred ECG electrodes of this invention include flexible highly-conductive material that can establish electrical contact with a subject without the use of conductive fluids, gels, pastes, and the like. The conductive material is usually in the shape of a single, elongated, rectangle or strip that is preferably bounded by a selvage edge. Other shapes, e.g., circle-like, ellipse-like, square-like, and so forth, can be used in different embodiments. Conductive fabrics are suitable electrode materials, and characteristics of preferred conductive fabrics are illustrated in FIGS. 4A-B, which are enlarged views (approximately 4×) of a portion of a conductive strip of an ECG electrode. As illustrated, suitable fabrics are woven (or knitted or the like) from fine conductive fibers such as metal wire or metal-coated fiber, metal-impregnated fiber, and the like. Also, preferred conductive fabrics are unaffected by normal textile processing steps (e.g., weaving, knitting, sewing), have the look and feel of normal textiles when woven or knitted, and are sufficiently durable for at least months of monitoring use. Preferred conductive fabrics are available from Textronics™ Inc., Wilmington, Del.

FIG. 3A illustrates, along with an embodiment of backbone construction, a first preferred electrode construction, where the electrode and conductive fabric strip are represented by the dashed line. This conductive fabric strip is attached (e.g., by sewing) onto a surface of the backbone fabric so that it follows the folding of the backbone. The electrode is exposed 8 on inner surface 3; then is folded 12 back the supporting backbone; then forms a tab-like portion 13 on the surface of flap 7. FIG. 3B also illustrates electrodes 8 hidden on the inner surface 3 and tabs 13 before and after folding back onto flap 7. FIGS. 5A-B also illustrate that electrode 8 is exposed on inner surface 3, and then folded 12 to form a tab-like portion 13 on flap 7.

Figure 8A:
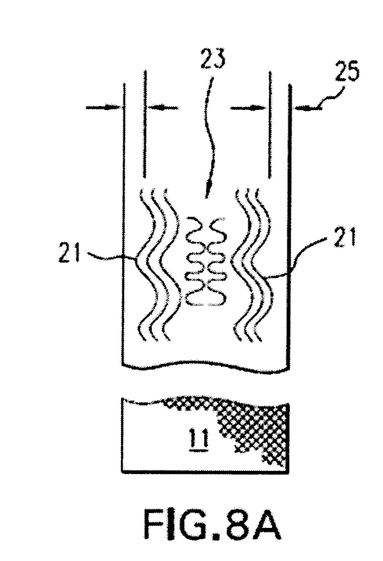
FIG. 8A-C illustrate views of an exemplary RIP sensor for use in this invention.

FIG. 3A also illustrates that signals from a fabric electrode are conveyed externally by conductive snap-type or button-like connector 9 (e.g., a mini-anorak type connector) affixed to the electrode and lead 10 from the button-like connector. As apparent in FIG. 4B (and FIG. 5A), connector 9 directly contacts many conductive fibers in the electrode material; connection to the remaining fibers is mediated by fiber contacts and crossings in the conductive fabric. Lead 10 from the button-like connector 9 is shown in FIG. 8C. Preferably, lead 10 is one of the conductors incorporated in RIP sensor 11, or contacts (e.g., by soldering and the like) one such conductor. RIP sensor 11 is represented in FIGS. 3B and 8A by a dash-dot line, and an exemplary RIP sensor is visible in FIG. 8C. Utilizing RIP sensor conductors for ECG sensor signals (and signals from other sensors) simplifies band construction because then separate leads for sensors need not be installed and because cable 1c then need only connect to conductors of the RIP sensor and not to separate conductors leading to other sensors. Specifically, an ECG electrode signal is carried by a conductor 21 laterally located in the RIP sensor.

FIGS. 6A-B illustrate another preferred embodiment of the ECG electrodes of this invention. This embodiment is substantially similar to the embodiment of FIG. 3A but with the principle exception of the presence of a thin strip of pillow material 14 between the inner surface 3 of a band and an ECG electrode 8 attached to this surface. This underlying pillow material serves to gently urge the electrode into contact with a wearer's skin. The pillow material is preferably, therefore, soft and flexible and, like the backbone cloth, is resistant to sweat and skin microorganisms. To improve electrical contact between then conductive fabric of an electrode and a subject's skin, it is also preferable that the pillow material be moderately water absorptive or retentive. Then, an amount of conductive sweat can be comfortably maintained between the conductive fabric and the subject's skin. Excessive water absorption or retention can lead to certain discomfort due to electrode saturation (especially during vigorous activity), and is thus not preferred.

The choice of backing material generally depends on a balance of fit, structural characteristics, moisture absorption and comfort. Such backing material might be, for example, 6 mm Neoprene polymer, available from Foamorder.com (www.foamorder.com). Others examples include, but are not limited to, Ethylene Propylene Diamine Monomer (EPDM) F-003091, Ethylene Vinyl Acetate (EVA) F-011400, and Neoprene/EPDM/SBR blend F-002032, all available from Armacell (www.armacell.com). While the above examples reference certain commercially available products, it should be kept in mind that other materials may also suffice.

Figure 7A:
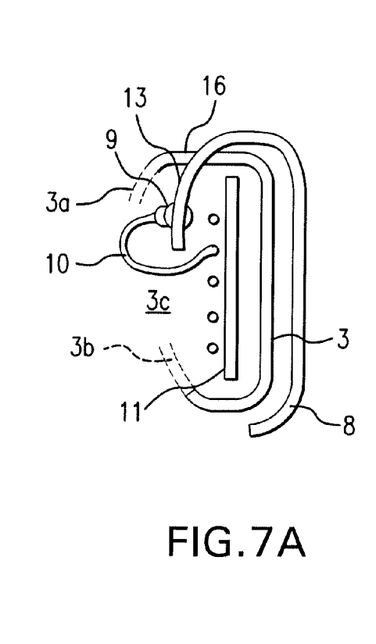
FIG. 7A-B illustrate a further preferred embodiment of an ECG electrode.
Figure 7B:
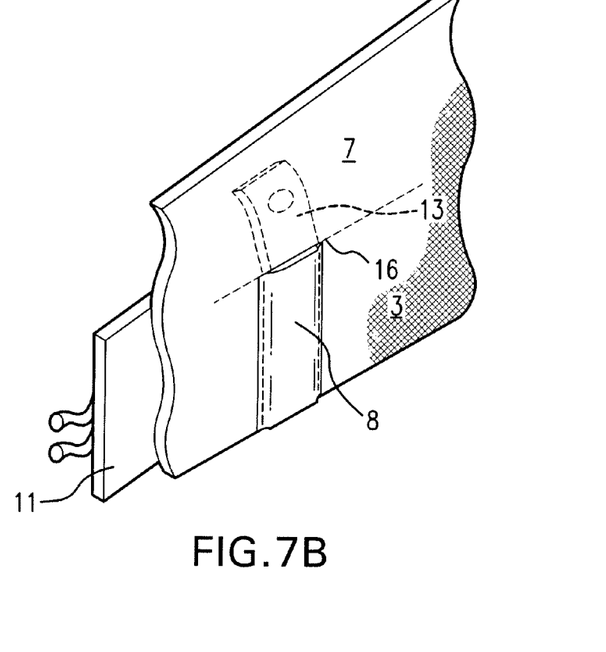

FIGS. 7A-B illustrate another preferred embodiment of the ECG electrodes of this invention which is suitable for another preferred folding pattern of the backbone material. In this embodiment, the backbone fabric is folded into a single pouch or single recess or single pocket that contains both the RIP sensor 11 and the ECG electrodes extensions 13 to which connection is made. FIG. 7A illustrates an exemplary such folding where the fabric inner surface 3 is formed between two longitudinal folds, and where the first flap 3a and second flap 3b of backbone material beyond these longitudinal folds meet each other so that tube-like interior pouch 3c is formed. The ECG electrode is again a single elongated strip of conductive fabric affixed (e.g., by sewing) onto the backbone fabric so that electrode 8 is exposed on inner surface 3 of the band. The electrode tab for external connection extends into internal pouch 3c through a short slit 16 (the width of the electrode) in the backbone material along one longitudinal told. Connection to the electrode can be as in the previous embodiment, namely through a button-like connector to a lead derived from one of the RIP sensor conductors.

A further variant is to include, as in FIGS. 6A-B, a strip of pillow-like material between the inner surface of the band and the ECG electrode.

Figure 8B:
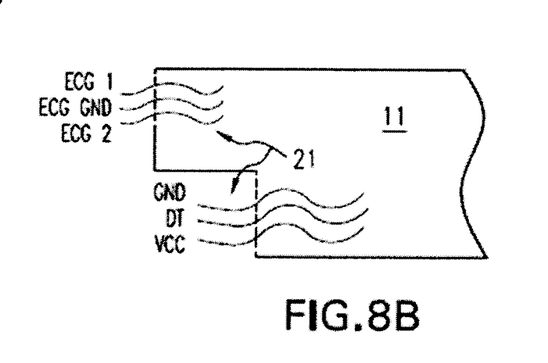
Figure 8C:
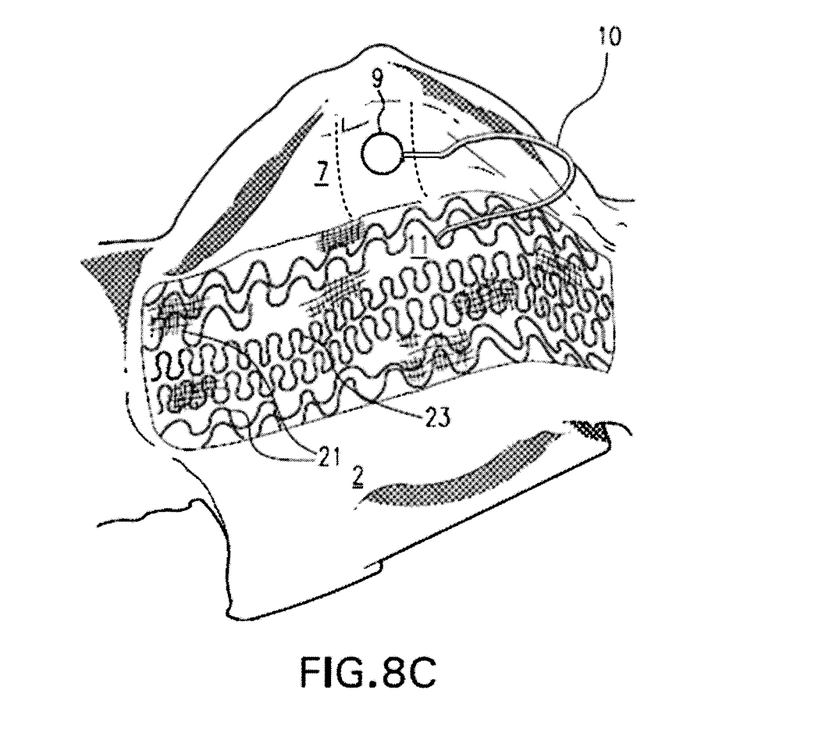

FIGS. 8A-B illustrate an exemplary respiratory inductive plethysmographic (RIP) sensor 11, and FIG. 8C illustrate a portion of an actual example of the RIP sensor similar to the RIP sensor of FIGS. 8A-B. Band-like garments of this invention provide respiratory sensors, preferably RIP sensors. A RIP sensor is held in a protected portion of a band, such as within folds of backbone material as in FIGS. 3A and 6A. The sensor is held so that it is tensioned by adjusting the band about a subject, and so that is moves along with respiratory and/or cardiac motions of the subject's chest. A band may have one or more RIP sensors. If only one RIP sensor is provided, it is preferably substantially the same length as the active section of the band. A band may alternatively include other plethysmographic type sensors based on changes in capacitance, resistance, mutual inductance, or other electrical property (or other property) that occur with changes in length or tension.

FIG. 8A illustrates schematically an exemplary preferred RIP sensor 11 in the form of an elastic band incorporating several conductors. The central portion of the band incorporates unshielded conductors 23 in a repetitive pattern at 5-6 spatial cycles per inch chosen for RIP performance. Laterally from the central RIP conductors are groups of conductors 21 in a repetitive pattern at 2-3 spatial cycles per inch chosen to limit conductor length and weight. These lateral conductors advantageously provide power and data leads to other sensors. FIG. 8B illustrates an exemplary use of lateral conductors 21: a first ECG sensor (ECG 1), a second ECG sensor (ECG 2), an ECG ground sensor (ECG GND), a lead for data from another sensor (DT), and power and ground (VCC, GND). Finally, the band is edged with a selvage edge 25. FIG. 8C illustrates a band constructed to be substantially similar to the band of FIG. 8A. Preferred RIP sensors are further described in U.S. patent application Ser. No. 11/233,317, filed Sep. 21, 2005, which is incorporated by reference herein in its entirety.

Figure 9:
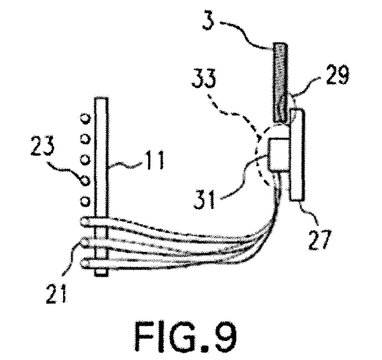
FIG. 9 illustrates a preferred mounting for a skin temperature sensor.

Bands of this invention can provide for additional physiology or physiology-related sensors, one example being an accelerometer and another being a skin temperature sensor. FIG. 9 illustrates an embodiment of a skin temperature sensor 33. Sensor 33 includes thermistor or more fully integrated temperature sensor 31 (e.g., proportional-to-absolute-temperature (PTAT) type circuitry) in an eline-type package which is bonded to metallic disk using thermally-conductive epoxy 27. The disk is sewn, glued, or otherwise bonded at 29 on the subject-facing surface of inner side material of a band. Lead wires to the thermistor skin temperature sensor are derived for a lateral group of conductors 21 of a RIP sensor 11, and are attached to the sensor by, e.g., soldering. The thermally conductive disk with supported thermistor and lead wires are coated for protection.

A band/strap garment of this invention and (optional) over-the-shoulder strap can be comfortably worn by subject's with a range of check sizes. First, as described, a band/strap garment is provided with an adjustment section for adjusting the band's length about a subject's chest. Second, as now described, the over-the-shoulder strap and its mountings flexibly accommodate to a range of chest sizes. Preferably, the over-the-shoulder strap itself is made of flexible materials and has an adjustable length so subject awareness of the strap is limited or minimal. For example, length adjustment means can be at the front or back buckle attachments. Also the front and back buckles that attach the over-the-shoulder strap permit attachment of a over-the-shoulder strap at adjustable positions on a band, and also permit free angular movement of an over-the-shoulder strap that is fixed to the buckles.

Figure 10A:
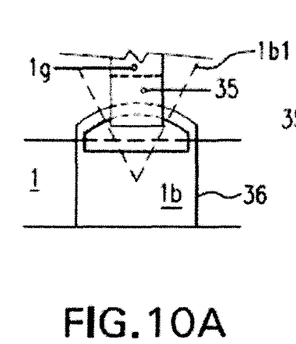
FIG. 10A-B illustrate one preferred buckle arrangement.
Figure 10B:
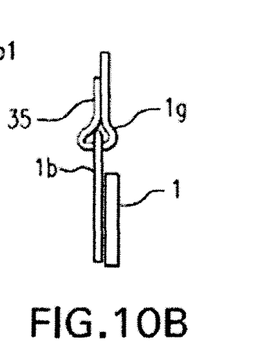

FIGS. 10A-B illustrate a plain view and a cross section of a preferred structure for rear buckle 1b (see also FIGS. 1A-B). The rear buckle is stitched to band 1 and provides an attachment site for over-the-shoulder strap 1g. The preferred attachment site permits the terminal portion of the over-the-shoulder strap to move freely through angle indicated at 1b1. In the illustrated embodiment, such angled movement is possible because opening of the rear buckle, through which the terminal portion of the over-the-shoulder strap passes, is larger than the terminal portion and has a curved shape which is convex towards band 1. The terminal portion of the over-the-shoulder strap passes through the buckle of the rear buckle, and then folds and is held to the over-the-shoulder strap by Velcro®, snaps, or other attachments suitable for fabric materials.

Figure 11A:
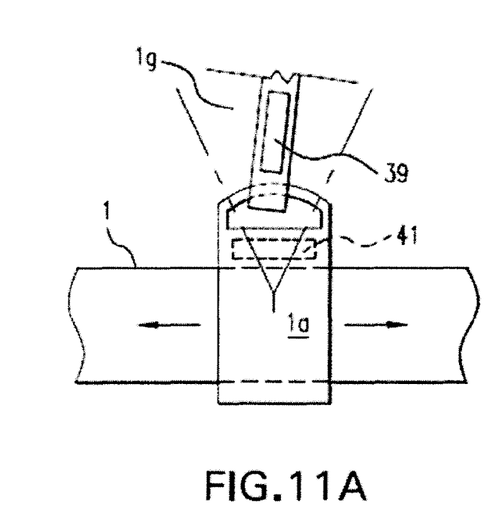
FIG. 11A-B illustrate another preferred buckle arrangement.
Figure 11B:
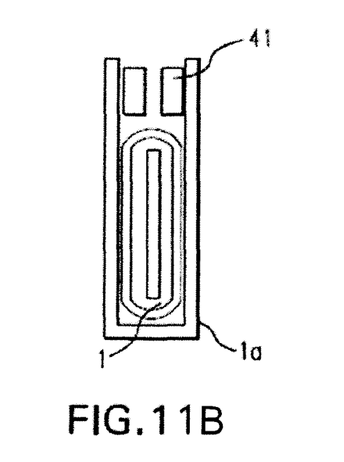

FIGS. 11A-B illustrate a preferred structure for front buckle 1a (see also FIGS. 1A-B). The front buckle has an opening structured similar to the opening of rear buckle 1b so that the over-the-shoulder strap can move freely in the front buckle through the indicated angle. The terminal portion of the over-the-shoulder strap is affixed to the front buckle by being folded back after passing through the buckle's opening being held by Velcro®, snaps, or other attachments suitable for fabric materials.

However, front buckle 1a is not permanently fixed to band-like garment 1, but can instead be adjusted back-and-forth along the band. Such adjustment is indicated in FIG. 11A. FIG. 11B illustrates that the front buckle has a U-shape that surrounds band 1 (illustrated as backbone fabric material enclosing a sensor, such as a RIP sensor). The legs of the U-shaped front buckle extend above the band and can be affixed to each other above the band by Velcro 41, snaps, or other attachments suitable for the buckle material. When the tops of the legs are not attached to each other, the buckle can freely move back-and-forth along band 1, but when the legs are attached, the buckle pinches the band is held in position. Alternatively, the tops of the legs are permanently attached (e.g., by adhesive) so that the buckle can be slid into a position from which it cannot readily move. A U-shaped portion of a front buckle can be plastic, fabric, and so forth. The width of the FB (indicated as "FBW") sufficient to limit adverse effects that the buckle may have on sensors incorporated into or carried by a band.

Figure 12:
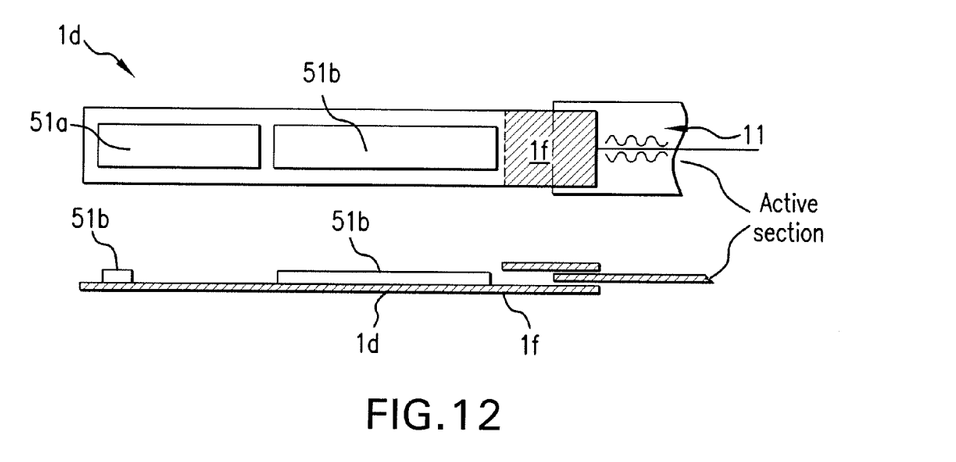
FIG. 12 illustrates a preferred adjustment section.

FIG. 12 illustrates plain and side views of details of a preferred adjustment portion. At the right of the band-like garment is the active section with RIP sensor 11. The left includes the adjustment portion 1d (including, e.g., a webbing-type fabric material) which is passed through loop 1e (FIGS. 2, 3B) and then folded back and attached to itself so that the band-like garment is held at a selected length. The adjustment-section webbing is fixed to the active section by preferably sewing 1f. In the illustrated embodiment, the adjustment-section webbing is attached to itself by mating Velcro® strip 51a, after it has passed through buckle 1e, with Velcro® strip 51b, that has not passed through buckle 1e.

Figure 13A:
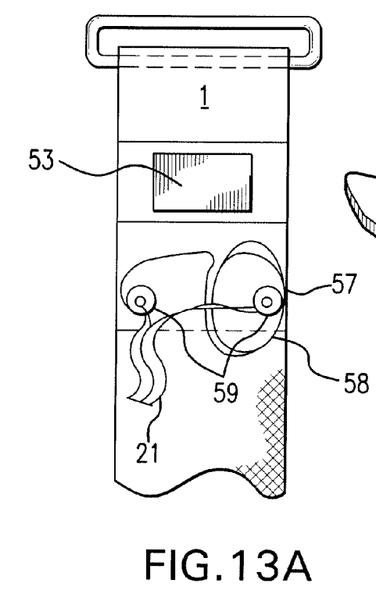
FIG. 13A-B illustrates alternative sensor attachments.
Figure 13B:
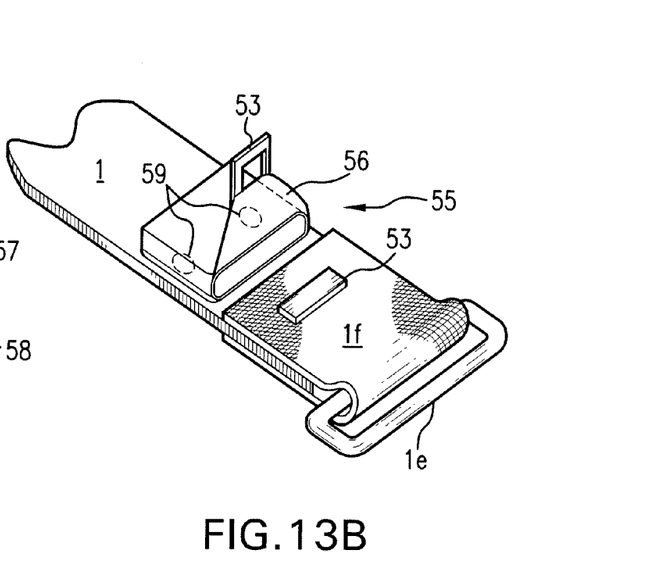

FIGS. 3A, 6A and 8C illustrate preferred attachments for ECG electrodes of this invention to leads derived from RIP sensor bands. FIGS. 13A-B illustrate attachment of alternative cardiac sensors. Alternative sensors may be attached and carried by a band/strap garment of this invention by various means including adhesive; sewing, Velcro®, snaps, and the like. FIG. 13B illustrates a pouch 55 for holding and carrying one or more sensors. The pouch is in turn attached to and carried by band 1. It can be sized to accommodate one or more alternative cardiac sensors (or types of physiological sensors). It can optionally include a flap-like top 56 for holding and protecting sensors carried in the pouch. In this embodiment, top 56 is held against band 1 by mating Velcro® strips 3. Also illustrated is buckle 1e for an adjustment section and attached by webbing to band 1 by sewing 1f.

FIG. 13A illustrates various alternative approaches to linking alternative cardiac (and other) sensors to leads derived from a RIP sensor band. In one approach, one, two, or more button-like conductive elements 59 (preferably of a type known as "mini-anorak") are linked to lateral conductors 21 incorporated into a RIP sensor band, e.g., in a manner similar to that illustrated in FIG. 8C and are attached to similar button-like conductive elements 59 interior to pouch 55. Sensors in the pouch can contact elements 59 and thereby to lateral conductors 21. Another approach is suitable for sensors that signal detected events by emitting a burst of electromagnetic fields which can be inductively received. Loop 58 is such an inductive receiver including loops of wire the ends of which are linked to button-like conductive elements 59 and then to leads 21 derived from a RIP sensor band. For sensors known in the art as "Polartech", a suitable receiver includes 10 to 14 loops of AWG 26 wire. In this approach, button-like conductive elements within carrying pouch (59 in FIG. 13B) are not directly connected to a sensor. Alternatively, both approaches can be combined when sensors include at least one sensor of each type.

The invention described and claimed herein is not to be limited in scope by the preferred embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

A number of references are cited herein, the entire disclosures of which are incorporated herein, in their entirety, by reference for all purposes. Further, none of these references, regardless of how characterized above, is admitted as prior to the invention of the subject matter claimed herein.

What is claimed is:
1. A physiological monitoring garment comprising:
an active portion comprising:
a backbone fabric material; and
a respiratory inductive plethysmographic band carried by the backbone material, the respiratory inductive plethysmographic band comprising:
a first respiratory inductive plethysmographic conductor having a length;
a lead formed from a second respiratory inductive plethysmographic conductor positioned laterally from the first respiratory inductive plethysmographic conductor along the length;
one or more flexible conductive fabric strips, each of the respective one or more flexible conductive fabric strips forming an ECG electrode and being attached to the backbone material, the one or more

ECG electrodes being electrically connected to the lead such that the lead is configured to carry ECG electrode signals; and one or more accessory leads, and wherein at least one of the one or more ECG electrodes is linked to at least one of the one or more accessory leads.

2. The garment of claim 1 wherein at least one of the one or more ECG electrodes further comprises an elastic and foam-like material that is adapted to urge the conductive fabric against a subject's skin.

3. The garment of claim 1 further comprising a skin temperature sensor linked to the accessory conductors of the respiratory inductive plethysmographic band.

4. The garment of claim 1 further comprising an adjustment section attached to ends of the active portion for snugly fitting the garment about a subject.

5. The garment of claim 1 wherein the adjustment section further comprises a tensioning belt adapted to link the active portion to encircle a wearer's torso.

6. The garment of claim 1 further comprising an adjustable over-the-shoulder strap.

7. The garment of claim 6 wherein the over-the-shoulder strap is linked to the garment by one or more buckles.

8. The garment of claim 7 wherein the over-the-shoulder strap is linked to at least one of the one or more buckles so as to permit angular motion of the over-the-shoulder strap with respect to the at least one buckle.

9. The garment of claim 7 comprising one buckle, of the one or more buckles, fixedly attached to the backbone material and one buckle, of the one or more buckles, slideably attached to the backbone material.

10. The garment of claim 1 further comprising a pouch attached to the respiratory inductive plethysmographic band.

11. The garment of claim 10, wherein the pouch is configured to hold one or more cardiac sensors.

12. A physiological monitoring garment comprising:
an active portion comprising a backbone fabric material folded onto itself so as to form a longitudinal-elongated recess; and
a respiratory inductive plethysmographic band arranged in the longitudinal-elongated recess of the backbone material, the respiratory inductive plethysmographic band comprising:
a first respiratory inductive plethysmographic conductor having a length;
a lead formed from a second respiratory inductive plethysmographic conductor positioned laterally from the first respiratory inductive plethysmographic conductor along the length;
one or more ECG electrodes attached to the backbone material comprising a flexible conductive fabric, an ECG electrode of the one or more ECG electrodes being electrically connected to the lead such that the lead is configured to carry ECG electrode signals; and
one or more accessory leads, and wherein at least one of the one or more ECG electrodes is linked to at least one of the one or more accessory leads.

13. The garment of claim 12,
wherein the flexible conductive fabric of the one or more ECG electrodes comprises:
a first portion being mounted on an exposed face of the folded backbone material and adapted to be in contact with a subject wearing the garment; and
a second portion having an electrical contact for attachment to the one or more leads, the second portion being arranged in the longitudinal-elongated recess of the backbone material so as not to be externally accessible,
wherein the folded backbone material comprises a single fold joining two longitudinally-elongated portions,
wherein the first portion of the at least one of the one or more ECG electrodes is mounted on the external face of one longitudinally-elongated portion of the backbone material, and
wherein the second portion of the at least one of the one or more ECG electrodes is mounted on the internal face of the other longitudinally-elongated portion of the backbone material.

14. The garment of claim 13 wherein the respiratory inductive plethysmographic band further comprises one or more accessory leads, and wherein at least one of the one or more ECG electrodes is linked to at least one of the one or more accessory leads.

15. The garment of claim 13, wherein the flexible conductive fabric is woven from conductive fibers.

16. The garment of claim 12 wherein the folded backbone material comprises two single folds joining three longitudinally-elongated portions, so that one internal longitudinally-elongated portion is arranged between the two external longitudinally-elongated portions,
wherein the first portion of the at least one of the one or more ECG electrodes is mounted on the external face of one of the external longitudinally-elongated portions of the backbone material, and
wherein the second portion of the at least one of the one or more ECG electrodes is mounted on the internal longitudinally-elongated portion.

17. The garment of claim 12 wherein the first respiratory inductive plethysmographic conductor is arranged on the respiratory inductive plethysmographic band in a pattern with a spatial frequency of 5-6 cycles per inch, and wherein the lead is arranged on the respiratory inductive plethysmographic band in a pattern with a spatial frequency of 2-3 cycles per inch.

18. The garment of claim 12 wherein the backbone material is elastic.

19. The garment of claim 18 wherein the backbone material comprises elastane.

20. A physiological monitoring garment comprising:
an active portion comprising:
a backbone fabric material folded onto itself;
an outer covering;
a respiratory inductive plethysmographic band supporting a plurality of respiratory inductive plethysmographic conductors having a length, a subset of the plurality of respiratory inductive plethysmographic conductors configured as a plurality of leads comprising an accessory lead, the plurality of leads being positioned laterally from the plurality of respiratory inductive plethysmographic conductors along the length;
a plurality of ECG electrodes being electrically connected to the plurality of respiratory inductive plethysmographic leads such that the plural respiratory inductive plethysmographic leads are configured to carry ECG electrode signals, each of the respective plurality of ECG electrodes having a plurality of conductive fibers woven to form a flexible conductive fabric, the flexible conductive fabric having a first portion mounted on an exposed face of the backbone material and a second portion mounted on an internal flap of the folded backbone material;

wherein the first portion is configured to contact a subject wearing the garment, wherein the second portion is not externally accessible, and wherein the plurality of ECG electrodes are electrically linked to the accessory lead by an electrical contact on the second portion, and the accessory lead is electrically linked to electronic processing circuitry, and a skin temperature sensor electrically linked to the accessory lead;

an adjustment portion attached to ends of the active portion and comprising a tensioning belt comprising linking the active portion to encircle a wearer's torso; and an over-the-shoulder strap for stabilizing the active portion on a wearer, and a front and a back buckle for attaching between the active and/or adjustment portions and the over-the-shoulder strap.

21. The garment of claim 20 further comprising an electronics module electrically linked to the respiratory inductive plethysmographic leads, the ECG electrodes, and the skin temperature sensor.

22. The garment of claim 20 wherein at least one of the plurality of ECG electrodes comprise an electrically conductive cloth for contacting the skin of a wearer.

* * * * *